United States Patent [19]

Narayanan et al.

[11] Patent Number: 5,130,131
[45] Date of Patent: Jul. 14, 1992

[54] METHODS FOR THE CONTROL OF FUNGI AND BACTERIA

[75] Inventors: Komaratchi R. Narayanan; Robert T. McMillan, Jr., both of Homestead, Fla.

[73] Assignee: University of Florida, Gainesville, Fla.

[21] Appl. No.: 395,625

[22] Filed: Aug. 18, 1989

[51] Int. Cl.$^5$ .............................................. A61K 37/547
[52] U.S. Cl. ................................. 424/94.65; 424/94.63
[58] Field of Search ........................... 424/94.63, 94.65

[56] References Cited

FOREIGN PATENT DOCUMENTS

| 0184288 | 6/1986 | European Pat. Off. |
| 53-029911 | 3/1978 | Japan |
| 54-073182 | 6/1979 | Japan |
| 90/03732 | 4/1990 | World Int. Prop. O. |

OTHER PUBLICATIONS

Pohronezny, K., V. H. Waddill, D. J. Schuster, and R. M. Sonoda (1986) "Integrated pest management for Florida tomatoes," *Plant Dis.* 70:96–102.

Pohronezny, K., and R. B. Volin (1983) "The effect of bacterial spot on yield and quality of fresh market tomatoes," *HotScience* 18:69–70.

Asahi Denka Kogyo, K.K. (1982) "Protein-decomposing enzymes as fungicides," Chemical Abstracts 97(13):202 (abstract 105601c).

Sawazaki, T., K. Ikeda, T. Misato, Y. Honma (1977) "Enzymic fungicides," Chemical Abstracts 87(11):160 (abstract 79669c).

*Primary Examiner*—Douglas W. Robinson
*Assistant Examiner*—Jean C. Witz
*Attorney, Agent, or Firm*—Saliwanchik & Saliwanchik

[57] ABSTRACT

The subject invention pertains to novel compositions which can be used to control fungi and bacteria. Methods of use are also described. Specifically exemplified are methods and compositions for control of certain fungal and bacterial plant pathogens.

9 Claims, No Drawings

METHODS FOR THE CONTROL OF FUNGI AND BACTERIA

DESCRIPTION

BACKGROUND OF THE INVENTION

One of the major problems facing the agriculture industry is the control of insect pests and disease. Of the many diseases which affect plants, a great number are of bacterial or fungal origin. Fungal and bacterial plant diseases can be especially problematic in hot, humid climates such as that which exists in Florida and other southern areas.

An example of an important vegetable disease caused by bacterial is bacterial leaf spot caused by *Xanthomonas campestris* pv *vesicatoria*. This pathogen causes widespread disease affecting Florida tomatoes (Pohronezny, K., V. H. Waddill, D. J. Schuster, and R. M. Sonoda [1986] Plant Dis. 70:96-102). Yield losses of up to 30% due to bacterial leaf spot have been reported (Pohronezny, K., and R. B. Volin [1983] HortScience 18:69-70).

Control efforts to date have focused on the identification of chemical control agents. At the present time, registered commercial pesticide sprays do not provide an acceptable level of control of bacterial leaf spot. A combination of copper and mancozeb provides a limited amount of control, but it is primarily effective only at low disease pressure.

In addition to being largely ineffective, current efforts to control fungi and bacteria present the further disadvantages of polluting the environment and creating potential health hazards to agricultural workers and to consumers, who may be exposed directly to the chemicals during application or to residues which can remain on the crops. Additional problems associated with traditional chemical pesticides include the development of resistance in target species, detrimental effects of these chemicals on non-target species, and phytotoxic reactions by treated plants.

Because of the problems associated with the use of traditional fungicides and bactericides, safer and more effective methods of control for bacterial and fungi are clearly needed. This is true, not only for use on tomato crops, but also for other crop plants and for non-agricultural uses as well.

BRIEF SUMMARY OF THE INVENTION

The subject invention concerns the discovery that proteinases, especially sulfhydryl proteinases such as papain, bromelain, and ficin, are effective in controlling pathogenic bacterial and fungi. *Xanthomonas campestris* pv *vesicatoris*, *Fusarium oxysporum* F. sp. *lycopersici* biotype 3, *Verticillium alboatrum* biotype 2, and other bacterial and fungi were found to be effectively inhibited by several sulfhydryl proteinases including papain.

DETAILED DESCRIPTION OF THE INVENTION

The role of proteinases and proteinase inhibotors in plants is not thoroughly understood. Some of the roles assigned to proteinases include (a) storage protein breakdown, (b) intracellular protein turn over, (c) role in development including senescence, and (d) proteolytic modification of proteins (Ryan and Walker-Simmons, 1981).

It has been discovered that some plants such as *Ipomea batatas, Lycopersicon peruvianum, Solanum macranthum*, kudzu, and pigeon pea, which have tolerance to many bacterial and fungal diseases, also contain high levels of endogenous proteinase activity. In order to determine whether there was any casual relationship between the presence of proteinases and the observed resistance to certain pathogens, a number of experiments have been conducted to assess the efficacy of proteinases in controlling bacterial and fungi. These experiments have been conducted in vitro and in the field. In vitro tests demonstrated that sulfhydryl proteinases were very effective in inhibiting the growth of both fungi and bacterial. For example, the sulfhydryl proteinase known as papain significantly reduced the incidence and severity of bacterial leaf spot in detached leaves of tomato. Furthermore, it was found that papain reduced the incidence of bacterial leaf spot in whole plants in growth chamber experiments.

In further experiments, papain and two other proteinases were found to be highly effective in inhibiting the growth of fungi. The proteinases were found to be effective against Fusarium and Verticillium.

Importantly, the proteinases of the subject invention were found to actually increase marketable yield obtained from tomato plants treated with proteinase as compared to yields obtained from plants treated with bactericides comprising copper. This increase in marketable yield may reflect the lack of phytotoxicity of the proteinases. These experiments also show that the compounds of the subject invention are not degraded too rapidly to exert their beneficial effects. However, because these compounds are proteins, they should be environmentally safe because they will not persist in the environment.

The proteinases of the subject invention are effective antifungal and antibacterial agents when they are simply applied to the surface of a plant, such as on the leaves of the plant. To facilitate this application, the proteinases may be mixed with an appropriate liquid or powder agricultural carrier. Suitable liquid diluents or carriers for use in the conduct of this invention include water, petroleum distillates, or other liquid carriers, with or without various dissolved salts and surface active emulsifying and dispersing agents. These liquid compositions may be prepared by dissolving or dispersing a bactericidal or fungicidal amount of a proteinase in the appropriate biologically compatible diluent or carrier.

Solid compositions may be prepared by dispersing the desired proteinases in or on an appropriately divided carrier such as clay, talc, bentonite, diatomaceous earth, fuller's earth, and the like. When such formulations are used as wettable powders, biologically compatible dispersing agents such as liquosulfonates and various non-ionic, anionic, amphoteric, or cationic dispersing and emulsifying agents can be used.

Whether a liquid or solid carrier is used, the proteinases may be combined with other fungicidal, bactericidal, or pesticidal compositions, as well as with fertilizers and plant growth regulators, so long as these other compositions do not denature the proteinase or otherwise inhibit its activity. The proteinases may also be encapsulated or otherwise formulated so as to increase their longevity in the field. Techniques for such encapsulation are known in the art.

When applied to the surface of plants, the proteinases of the subject invention inhibit the growth of fungi and bacterial. These compounds are particularly useful with plants because they are not phytotoxic. In addition to their use on plants, the compounds of the subject invention may also be used on any other surface in need of a bactericidal or fungicidal agent. Also, the proteinases of the subject invention can be used as preservatives or sterilants of materials susceptible to microbial contamination.

MATERIALS AND METHODS

Plant Material.

All the plants used in this study were obtained from the Tropical Research and Education Center of the University of Florida at Homestead. Seeds of *Lycopersicon esculentum* L. cv Flora-Date were from the germ plasm collections and the Tropical Research and Education Center.

Chemicals.

Chemicals were purchased from Sigma Chemical Company and Fisher Scientific. All chemicals were of the highest purity available.

In vitro Inhibition Studies.

Purified papain was either dialyzed (to remove preservatives such as thymol) against 10 mM phosphate buffer, pH 7, containing dithiothreitol or used directly after dilution with buffer containing dithiothreitol. Spores of *Fusarium oxysporum* Schlecht biotype 3 were treated for 1 hour with 1, 10 mg/ml dialyzed papain, or 10 mg/ml of undialyzed papain at room temperature. After 1 hour, 100 ul of spore suspension was spread on plates. After 2–3 days, the plates were evaluated for growth of Fusarium.

Following are examples which illustrate procedures, including the best mode, for practicing the invention. These examples should not be construed as limiting. All percentages are by weight and all solvent mixture proportions are by volume unless otherwise noted.

EXAMPLE 1

Assay of Bacterial Leaf Spot in Detached Leaves

Fully expanded leaves from 5-week old *Lycopersicon esculentum* L. cv Flora-Date plants grown in the greenhouse were immersed in deionized water with the petioles submerged in water. With a brush, 0, 0.23, 2.3, or 23 units/ml of papain (2.3 units/mg of papain) was applied to the detached leaves of tomato. This was immediately followed by application of *Xanthomonas campestris* pv *vesicatoria* on the surface of all leaves. The leaves, in individual test tubes, were kept in the greenhouse for 2 weeks prior to evaluation for the incidence and severity of bacterial leaf spot. There were three replications consisting of 4 leaves for each treatment for each replication. The results of these experiments are shown in Table 1.

TABLE 1

Effect of thiol proteinase on severity of bacterial leaf spot in detached leaves of tomato

| Concentration of proteinase (units/ml) | # spots/leaf | % reduction in severity of disease |
|---|---|---|
| 0 | 49.3 ± 4.2 | 0 |
| 0.23 | 10.3 ± 3.7 | 79.1 |
| 2.3 | 4.1 ± 2.1 | 91.7 |
| 23.0 | 1.0 ± 0.3 | 98.0 |

A strong protective effect of papain against bacterial leaf spot was observed. Both the incidence and severity of bacterial leaf spot were reduced by treatment with papain. These experiments were successfully repeated on whole plants in the greenhouse. For the greenhouse experiments, the plants used were *Lycopersicon esculentum* cv 'Horizon.' The plants were 2 weeks old when they were infected with *Xanthomonas campestris* pv *vesicatoria* after spraying with papain at appropriate concentrations. There were 20 plants for each treatment with 2 replications. The plants were kept in a hot dew chamber for 2-3 days prior to evaluation. The results of this study are shown below in Table 2. Significant reductions in the number of lesions on these plants were seen when proteinase was applied.

TABLE 2

Effect of thiol proteinase on the incidence and severity of bacterial leaf spot in whole plants.

| Concentration of proteinase mg/ml | % plants with symptoms | # of lesions/$cm^2$ |
|---|---|---|
| 0 | 80 | 4.00 |
| | 75 | 3.10 |
| 1 | 20 | 0.40 |
| | 15 | 0.25 |
| 10 | 15 | 0.20 |
| | 10 | 0.10 |

EXAMPLE 2

Field experiments were conducted wherein papain was compared against copper/mancozeb applications in grower fields. The results of these field experiments are shown in Table 3. The field experiments were designed to assess the marketable yield which could be obtained from plants which were treated with proteinase as compared to plants which were treated with a copper and mancozeb mixture. The copper treatment is the form of control which is most widely practiced at the present time. The results of a test such as this are particularly illuminating because it indicates how well the control agent works under actual field conditions.

TABLE 3

| | Total marketable yield (lbs.) | | |
|---|---|---|---|
| Replication | Copper | Protease | % difference using protease |
| 1 | 1548 | 1781 | +15.0 |
| 2 | 1480 | 1648 | +11.4 |
| 3 | 1420 | 1717 | +20.9 |
| 4 | 1247 | 1858 | +49.0 |
| Average | 1424 | 1751 | +23.0 |

As can be seen in Table 3, the marketable yield obtained from plants treated with proteinase ranged from 11% to nearly 50% higher than the yield obtained after treatment with the copper mixture. This shows that proteinase is not only effective in inhibiting bacterial leaf spot, but also that plants treated with proteinase produce a greater marketable yield than plants treated with other compositions which control bacterial leaf spot. This enhanced yield may be due to the low phytotoxicity of proteinases as compared to the copper composition.

The success of these field experiments also clearly demonstrated that these proteins retained sufficient activity to exert their beneficial effects despite exposure to sunlight, wind, and rain. Advantageously, however, these compositions will not persist in the environment in the manner that many other pesticides do. Therefore, these control agents are both effect and environmentally safe.

EXAMPLE 3

Inhibition of *Fusarium oxysporum* Biotype 3 by Sulfhydryl Proteinases

Purified papain from Sigma Chemical Company (#P 3125) was either dialyzed (to remove preservatives such as thymol) against 10 mM, ph 7 phosphate buffer containing 1 mM dithiothreitol (DTT) or used directly after dilution with buffer containing DTT. Spores of *Fusarium oxysporum* biotype 3 were treated for 1 hour with 0, 10 mg/ml dialyzed papain, or 10 mg/ml undialyzed papain at room temperature. After 1 hour, 100 ul of spore suspension was spread on plates. After 2-3 days, the plates were evaluated for growth of Fusarium. Table 4 shows the effect of papain on *Fusarium oxysporum* biotype 3. The treatment of spores for 1 hour completely inhibited the growth of spores.

Other sulfhydryl proteinases were also tested for their effectiveness in inhibiting the formation of *Fusarium oxysporum* colonies. As can be seen in Table 4, other sulfhydryl proteinases were also very effective in preventing the formation of colonies, In the case of Bromelain, it was important that the proteinase was dialyzed. Dialyzation removes impurities, such as proteinase inhibitors which can adversely affect the performance of the proteinase.

TABLE 4

Effect of different sulfhydryl proteinases on *Fusarium oxysporum*

| Treatment | Blank | Bromelain | | Ficin | | Papain | |
| --- | --- | --- | --- | --- | --- | --- | --- |
| | | 1 | 2 | 1 | 2 | 1 | 2 |
| Control | 0* | 0 | 0 | 0 | 0 | 0 | 0 |
| Fusarium | 155 | 81.3 | 0.7 | 0 | 0 | 0 | 0 |

*no. of colonies;
1 = nondialyzed material;
2 = dialyzed material

We claim:

1. A method for inhibiting fungal or bacterial growth on plants, wherein said inhibited fungi or bacterial are selected from the group consisting of Fusarium, Xanthomonas, and Verticillium, said method comprising the application to the surface or situs of said plant a fungicidally or bactericidally effective amount of a composition comprising one or more proteinases, wherein said proteinase is papain or bromelain.

2. The method, according to claim 1, wherein said proteinase is papain.

3. The method, according to claim 1, wherein said plant is a vegetable crop plant.

4. The method, according to claim 1, wherein said plant is a tomato.

5. The method, according to claim 1, wherein said proteinase has been purified by dialysis.

6. The method, according to claim 1, wherein said proteinase is mixed with an agriculturally acceptable carrier or diluent.

7. The method, according to claim 1, wherein said proteinase has been encapsulated or otherwise modified to prolong its activity.

8. The method, according to claim 1, wherein said method is used to inhibit the growth of *Fusarium oxysporum*.

9. The method, according to claim 1, wherein said method is used to control *Xanthomonas campestris*.

* * * * *

UNITED STATES PATENT AND TRADEMARK OFFICE
CERTIFICATE OF CORRECTION

PATENT NO.    :    5,130,131

DATED         :    July 14, 1992

INVENTOR(S)   :    Komaratchi R. Narayanan, Robert T. McMillan, Jr.

It is certified that error appears in the above-identified patent and that said Letters Patent is hereby corrected as shown below:

Column 1:   line 16: "by bacterial is" should read --by bacteria is--; line 43: "control for bacterial" should read --control for bacteria--; line 52: "pathogenic bacterial" should read --pathogenic bacteria--; line 53: "pv vesicatoris" should read --pv vesicatoria--; line 55: "bacterial and fungi" should read --bacteria and fungi--; line 60: "proteinase inhibotors" should read --proteinase inhibitors--.

Column 2:   line 12: "fungi and bacterial" should read --fungi and bacteria--; line 68: "bacterial" should read --bacteria--.

Column 3:   line 14: "Flora-Date" should read --Flora-Dade--; line 25: "dithiothreitol" should read --dithiothreitol.--; line 27: "with 1" should read --with 0--; line 41: "Flora-Date" should read --Flora-Dade--.

Column 4:   line 62: "demonstrated" should read --demonstrates--.

Column 5:   line 26: "colonies," should read --colonies.--

Column 6:   line 12: "bacterial" should read --bacteria--.

Signed and Sealed this

Twenty-fourth Day of August, 1993

Attest:

BRUCE LEHMAN

Attesting Officer

Commissioner of Patents and Trademarks